US012741068B2

(12) United States Patent
Cheng et al.

(10) Patent No.: US 12,741,068 B2
(45) Date of Patent: Sep. 22, 2026

(54) METHOD FOR MANUFACTURING MITOCHONDRIA-RICH PLASMA

(71) Applicant: TAIWAN MITOCHONDRION APPLIED TECHNOLOGY CO., LTD., Zhubei City (TW)

(72) Inventors: Han-Chung Cheng, Zhubei City (TW); Chih-Kai Hsu, Zhubei City (TW); Hui-Ching Tseng, Zhubei City (TW); An-Ling Cheng, Zhubei City (TW)

(73) Assignee: TAIWAN MITOCHONDRION APPLIED TECHNOLOGY CO., LTD., Zhubei City (TW)

( * ) Notice: Subject to any disclaimer, the term of this patent is extended or adjusted under 35 U.S.C. 154(b) by 591 days.

(21) Appl. No.: 17/948,764

(22) Filed: Sep. 20, 2022

(65) Prior Publication Data

US 2023/0016499 A1 Jan. 19, 2023

Related U.S. Application Data

(63) Continuation-in-part of application No. PCT/CN2021/082117, filed on Mar. 22, 2021.

(Continued)

(51) Int. Cl.

| | |
|---|---|
| ***A61M 1/02*** | (2006.01) |
| ***A61K 35/12*** | (2015.01) |
| ***A61K 35/16*** | (2015.01) |
| ***A61K 35/19*** | (2015.01) |
| ***A61K 35/28*** | (2015.01) |
| ***A61K 38/36*** | (2006.01) |
| ***A61M 1/36*** | (2006.01) |
| ***A61P 13/12*** | (2006.01) |

(Continued)

(52) U.S. Cl.

CPC ............. *A61M 1/029* (2013.01); *A61K 35/12* (2013.01); *A61K 35/16* (2013.01); *A61K 35/19* (2013.01); *A61K 35/28* (2013.01); *A61K 38/36* (2013.01); *A61M 1/3693* (2013.01); *A61P 13/12* (2018.01); *A61P 17/02* (2018.01); *A61P 19/02* (2018.01); *A61P 19/04* (2018.01); *C12N 5/0018* (2013.01); *C12N 5/0605* (2013.01); *C12N 5/0667* (2013.01); *C12N 2500/84* (2013.01); *C12N 2501/998* (2013.01); *C12N 2502/115* (2013.01)

(58) Field of Classification Search

CPC .... A61K 2300/00; A61K 35/12; A61K 35/14; A61K 35/16; A61K 35/19; A61K 35/28; A61K 38/00; A61K 38/36; A61M 1/029; A61M 1/3693; A61P 13/12; A61P 17/02; A61P 17/14; A61P 17/18; A61P 19/02; A61P 19/04; A61P 21/00; A61P 43/00; C12N 2500/84; C12N 2501/998; C12N 2502/115; C12N 5/0018; C12N 5/0605; C12N 5/0667

See application file for complete search history.

(56) References Cited

U.S. PATENT DOCUMENTS

2017/0151287 A1* 6/2017 von Maltzahn ........ A61K 35/19
2017/0290763 A1* 10/2017 Su ........................ A61K 9/0019

* cited by examiner

*Primary Examiner* — Dirk R Bass
(74) *Attorney, Agent, or Firm* — Maschoff Brennan

(57) ABSTRACT

The embodiments of the present disclosure provide a manufacturing method of mitochondria-rich plasma. The mitochondria-rich plasma can increase the cell viability of damaged cells, decrease the cellular senescence level, repair the oxidative damage of cells, and relieve the inflammation of hair follicles so as to achieve the purpose of promoting hair regrowth.

3 Claims, 10 Drawing Sheets
(3 of 10 Drawing Sheet(s) Filed in Color)

Related U.S. Application Data

(60) Provisional application No. 62/992,546, filed on Mar. 20, 2020.

(51) Int. Cl.

| | |
|---|---|
| ***A61P 17/02*** | (2006.01) |
| ***A61P 19/02*** | (2006.01) |
| ***A61P 19/04*** | (2006.01) |
| ***C12N 5/00*** | (2006.01) |
| ***C12N 5/073*** | (2010.01) |
| ***C12N 5/0775*** | (2010.01) |

METHOD FOR MANUFACTURING MITOCHONDRIA-RICH PLASMA

CROSS-REFERENCE TO RELATED APPLICATIONS

This application is a continuation-in-part of International Application No. PCT/CN2021/082117, filed on Mar. 22, 2021, which claiming priority to U.S. provisional patent application Ser. No. 62/992,546, filed on Mar. 20, 2020, the entire contents of which are hereby incorporated by reference.

BACKGROUND

1. Technical Field

The present disclosure relates to a method for manufacturing mitochondria-rich plasma.

2. Related Art

Hair follicles are an important organ for hair growth. The activation cycle of the hair follicles includes multiple phases from telogen, anagen to catagen, and finally back to telogen. Hair grows and falls in the cycle. The hair follicles are most active in anagen phase. Hair follicle dermal papilla cells (HFDPC) located at the root of the hair grow massively in anagen phase and transfer signals to the surrounding stromal cells to promote the stromal cells to proliferate and differentiate to form the hair.

When the hair follicles are damaged or aging, the hair growth is affected. Specifically, the symptoms include brittle hair, slow growth, sparse hair, or even no longer growth. The hair is not only for the appearance but also has many effects, such as heat insulation, keeping warm, and protection, depending on different parts. For example, the eyelashes protect the eyes, and hair regulates the temperature of the head. If animals lack hair, it will not only affect the appearance, such as baldness, but also cause inconveniences and danger.

SUMMARY

In one embodiment of the present disclosure, a method for manufacturing mitochondria-rich plasma is provided, comprising: separating plasma and cells from blood; taking out mitochondria from the cells; and mixing the plasma and the mitochondria to form mitochondria-rich plasma.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The present disclosure will become more fully understood from the detailed description given hereinbelow and the accompanying drawings which are given by way of illustration only and thus are not limitative of the present disclosure and wherein.

DETAILED DESCRIPTION

Figure 1:
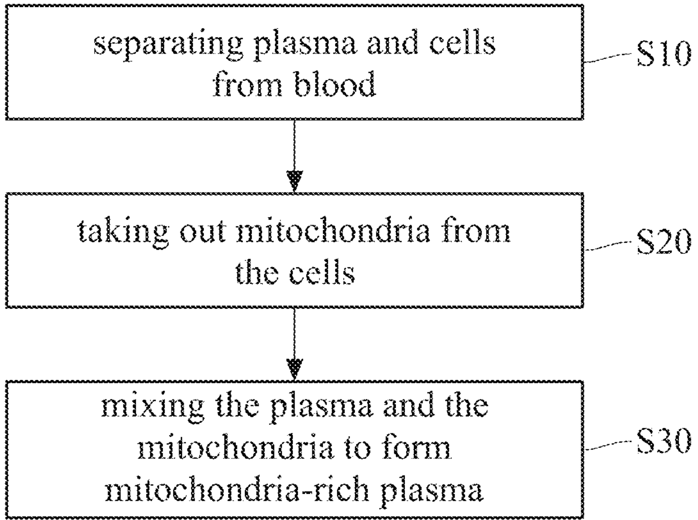
FIG. 1 is a flow chart of a method for manufacturing mitochondria-rich plasma according to one embodiment of the present disclosure.

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present disclosure. The following embodiments further illustrate various aspects of the present disclosure, but are not meant to limit the scope of the present disclosure.

Mitochondria are places where oxidative phosphorylation (OXPHOS) and adenosine triphosphate (ATP) synthesis occur. In addition to supplying the energy for normal cell metabolism, the mitochondria are also responsible for regulating the functions including dealing with the oxidative stress in cells, signaling, and so on. During hair growth, the abnormal mitochondria may cause problems in the hair follicles activation and hair growth. Therefore, the inventors repair the mitochondria in the hair follicles in a manner of replacing mitochondria so as to improve the damaged hair follicles and promote hair regrowth to.

According to one embodiment of the present disclosure, the composition for promoting hair regrowth includes mitochondria. The composition may contact the hair follicles or the skin around the hair follicles to promote hair regrowth in a manner of applying, coating, injecting, or directly dropping. In the composition, the concentration of the mitochondria may be 5 μg/mL to 200 μg/mL, but the present disclosure is not limited thereto. In other embodiments, the concentration of the mitochondria may be 40 μg/mL to 200 μg/mL. The solvent included in the composition may be a solvent that enables the mitochondria to maintain function and morphology thereof, for example, water, normal saline, phosphate solution, salt buffer, mannitol solution, sucrose solution, plasma, serum, platelet-rich plasma, and so on.

Mitochondria may be taken from animal cells, but the present disclosure is not limited thereto. The cells providing the mitochondria may include cells having mitochondria such as adipose stem cells, monocytes, embryonic stem cells, mesenchymal stem cells, hematopoietic stem cells, CD34+ stem cells, bone marrow stem cells, muscle cells, hepatocytes, skin cells, nerve cells, blood cells, and so on. In some embodiments, the mitochondria are preferably derived from cells of the same species as the person to whom the composition is administered. For example, if the person to whom the composition is administered is human, human cells are used, and if the person to be administered the composition is a dog, dog cells are used. In some embodiments, the mitochondria may also be exogenous mitochondria obtained from cells of the same or different species as the person to whom the composition is administered, preserved in vitro or cultured in vitro.

Hereinafter, the mitochondria used in the following experiments are described. The mitochondria used in the embodiment of the present disclosure are extracted from human adipose-derived stem cells (ADSC). The stem cell culture medium includes Keratinocyte SFM (IX) solution (Gibco), bovine pituitary extract (BPE, Gibco), and 10% (weight percentage concentration) of fetal bovine serum (HyClone). Firstly, the ADSCs are incubated in a cell culture dish until the number of the ADSCs reaches $1.5\times10^8$, and then rinsed with Dulbecco's phosphate-buffered saline (DPBS). Next, after DPBS is removed, trypsin is added for cell detachment and reacted with the cells at 37° C. for 3 minutes, and then the stem cell culture medium is added to stop the reaction. Next, the ADSCs are washed and then dispersed, and centrifuged at 600 g for 10 minutes, and the supernatant is removed. Next, the remained ADSCs and 80 mL of IBC-1 buffer (225 mM mannitol, 75 mM sucrose, 0.1 mM EDTA, 30 mM Tris-HCl pH 7.4) are added to a homogenizer, and then the ADSCs are ground 15 times on ice by the homogenizer. Next, the homogenized ADSCs are centrifuged at 1000 g for 15 minutes, and the supernatant is collected into another centrifuge tube. The collected supernatant is further centrifuged at 9000 g for 10 minutes, the supernatant obtained from the further centrifugation is removed, and the obtained pellets are the mitochondria. Next, 1.5 mL of IBC-2 buffer (225 mM mannitol, 75 mM sucrose, 30 mM Tris-HCl pH 7.4), protease inhibitor and the mitochondria are mixed and stored at 4° C.

According to the other embodiment of the present disclosure, the composition for promoting hair regrowth includes mitochondria and plasma. In the composition, the concentration of the mitochondria may be 5 μg/mL to 200 μg/mL, but the present disclosure is not limited thereto. In other embodiments, the concentration of the mitochondria may be 40 μg/mL to 200 μg/mL. In the composition, the number of platelets in the plasma may be less than $1\times10^4$ per μL. and the concentration (v/v %) of the plasma may be 5%.

Hereinafter, the plasma used in the following experiments is described. Firstly, fresh blood is drawn into a blood collection tube or a centrifuge tube containing anticoagulant, and the blood in the tube is centrifuged at 1500 to 2000 g for 10 minutes to stratify the blood to form an erythrocyte layer, a gel layer, a buffy coat layer, and a plasma layer. Next, the plasma layer is collected to obtain the plasma used in the embodiments. In the plasma obtained by the above method, the number of platelets in the plasma may be less than $1\times10^4$ per μL.

According to another embodiment of the present disclosure, the composition of mitochondria-rich plasma includes mitochondria and plasma. The plasma may include growth factors. The growth factors may include TGF-β1, PDGF-AA, PDGF-AB, or PDGF-BB. The concentration of TGF-β1 may be 3.1 mg/mL or more, the concentration of PDGF-AA may be 9.5 ng/mL or more, the concentration of PDGF-AB may be 91.7 ng/mL or more, and the concentration of PDGF-BB may be 79.3 ng/mL or more. The composition may contact the hair follicles or the skin around the hair follicles to promote hair regrowth in a manner of applying, coating, injecting, or directly dropping. In the composition, the weight of the mitochondria may be more than 5 μg.

According to another embodiment of the present disclosure, refer to FIG. 1, and FIG. 1 is a flow chart of a method for manufacturing mitochondria-rich plasma according to one embodiment of the present disclosure. The method for manufacturing mitochondria-rich plasma includes: separating plasma and cells from blood (S10); taking out mitochondria from the cells (S20); and mixing the plasma and the mitochondria to form mitochondria-rich plasma (S30). The step of separating plasma and cells from blood (S10) may include: stratifying the blood to form an erythrocyte layer, a buffy coat layer, and a plasma layer; and taking out the buffy coat layer and the plasma layer. The step of taking out mitochondria from the cells (S20) may include taking out the mitochondria from the cells in the buffy coat layer. The step of mixing the plasma and the mitochondria to form mitochondria-rich plasma (S30) may include mixing the plasma layer and the mitochondria. In addition, the step of taking out mitochondria from the cells (S20) may include: mixing the cells with an extraction buffer to form a mixture; sucking the mixture back and forth using a syringe and a needle to break the cells into cell debris to release mitochondria; and separating the cell debris and the mitochondria and collecting the mitochondria.

Hereinafter, the method of manufacturing mitochondria-rich plasma used in the following experiments is described. Firstly, 8 to 10 mL of blood is drawn to CPT tube (BD Vacutainer® CPT™ Cell Preparation Tube, REF362761), but the present disclosure is not limited thereto, any blood collection tube or centrifuge tube containing anticoagulant may be used. Next, the blood is centrifuged at 1500 g for 10 minutes to stratify the blood to form an erythrocyte layer, a gel layer, a buffy coat layer, and a plasma layer, wherein the buffy coat layer includes monocytes and platelets. Next, the plasma layer and the buffy coat layer is taken into a new centrifuge tube and centrifuged at 400 g for 5 minutes to stratify the plasma and cells, and the plasma is separated and collected to another centrifuge tube. Next, 1.5 mL of extraction buffer is added to the tube including the cells, and the cells are sucked back and forth using a 23G needle and a syringe to break the monocytes and the platelets, thereby releasing mitochondria. The extraction buffer may be a NaCl solution with osmolarity of 42.8 mOsm/L. Next, the cells after being sucked back and forth are centrifuged at 400 g for 5 minutes to stratify the cell debris and the mitochondria, and the supernatant including mitochondria is collected. The method for releasing mitochondria is not limited thereto, and a detergent, such as CHAPS detergent, Triton X-100, NP40, and so on, may be used to help the cells to release mitochondria. Next, the supernatant including the mitochondria is mixed with the above collected plasma, about 5 to 8 mL of mitochondria-rich plasma is obtained. In the mitochondria-rich plasma obtained by the above method, the weight of the mitochondria may be more than 5 μg.

Hereinafter, the cell used in the following experiments is described. Human hair follicle dermal papilla cell (HFDPC) is used as a cell model for studying hair follicle activation in Experiments 1 to 5. The culture conditions are as below, HFDPCs are cultured in the Follicle Dermal Papilla Growth Medium (PromoCell, C-26501) and placed in an incubator at the circumstance with 5% carbon dioxide at 37° C. When HFDPC is cultured to 90% full of the cell culture dish, the culture medium in the cell culture dish is removed, and the cells are rinsed by phosphate buffered saline (PBS). Next, PBS is removed, 0.25% trypsin is added to the cell culture dish and reacted for 5 minutes at 37° C., and then the reaction is stopped by adding the culture medium into the cell culture dish. Next, the cells and the cell culture medium are centrifuged at 1000 rpm (300 g) for 5 minutes, and then the supernatant is removed. Next, the fresh cell culture medium is added, and then the cells are counted. The subculture is performed depending on the experiment requirement.

Experiment 1: Cell Damage

Hydrogen peroxide ($H_2O_2$) and tert-butyl hydroperoxide (tBHP) are peroxide and are usually used as a substance for inducing cell damage, oxidation, senescence, and apoptosis. In this experiment, $H_2O_2$ and tBHP are used to damage HFDPCs, and the damage of HFDPCs are assessed by Alamar blue cell viability reagent kit and expressed by the cell viability.

Alamar blue is a reagent for assessing cell viability. Resazurin in the Alamar blue reagent is a redox indicator and is a deep blue dye that is non-toxic, permeable to the cell membrane, and low-fluorescent. When resazurin enters into the healthy cells, it is reduced to resorufin, which is pink and high-fluorescent, due to the reduced environment in the cells. The cell proliferation or cell viability may be assessed by measuring the absorbance or the fluorescence of resorufin. The higher the absorbance or the fluorescence of resorufin indicates the more cells and the higher cell proliferation or cell viability. The higher cell proliferation or cell viability indicates the healthier cells and the better proliferation ability. Therefore, Alamar blue is used as an indicator for assessing cell proliferation or cell viability in this experiment.

Hereinafter, the procedures of the experiment are described. HFDPCs after subculture are cultured at a density of $5\times10^4$ cells/500 μL in a 24-well plate for 8 hours. Next, the supernatant in the wells is removed, the cells are rinsed by PBS, the supernatant is removed again, and then 500 μL of the culture medium is added and incubated for 8 hours. Next, $H_2O_2$ or tBHP with different concentrations is added to the wells, and the cells are cultured for 4 hours in the presence of $H_2O_2$ or tBHP, in which the concentrations of $H_2O_2$ in the wells are 100 μM, 300 μM, and 500 μM, and the concentrations of tBHP in the wells are 100 μM, 200 μM, and 300 μM. Next, the supernatant in the wells is removed, and the cell culture medium is replaced with the medium including Alamar blue and further incubated at 37° C. for 3 to 4 hours. After cell culturing with the medium including Alamar blue, the cell viability is calculated by the fluorescence measured at OD560/590.

Figure 2:
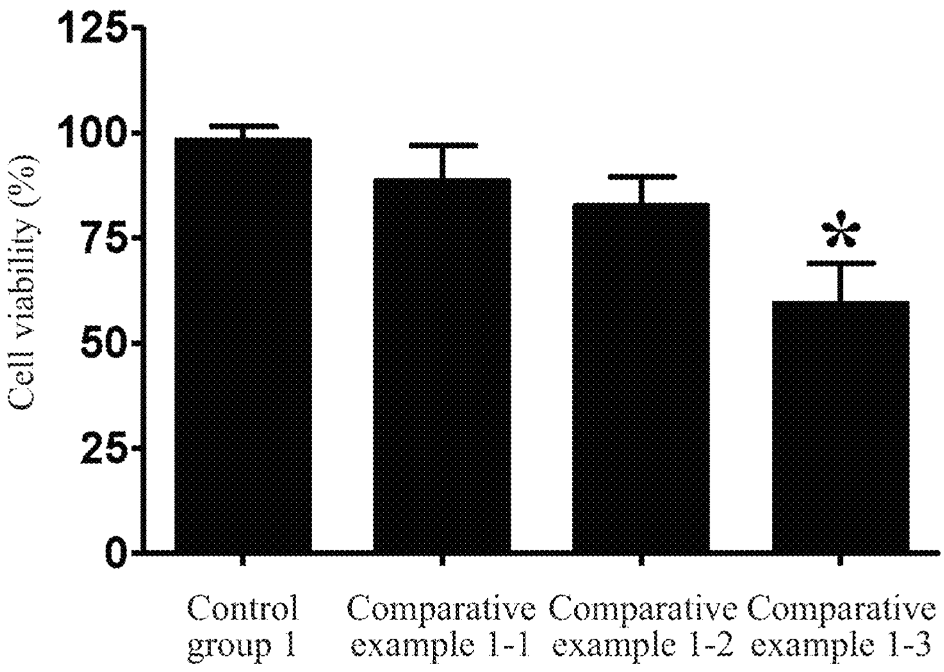
FIG. 2 shows the effect on the cell viability of HFDPC depending on different concentrations of tBHP.
Figure 3:
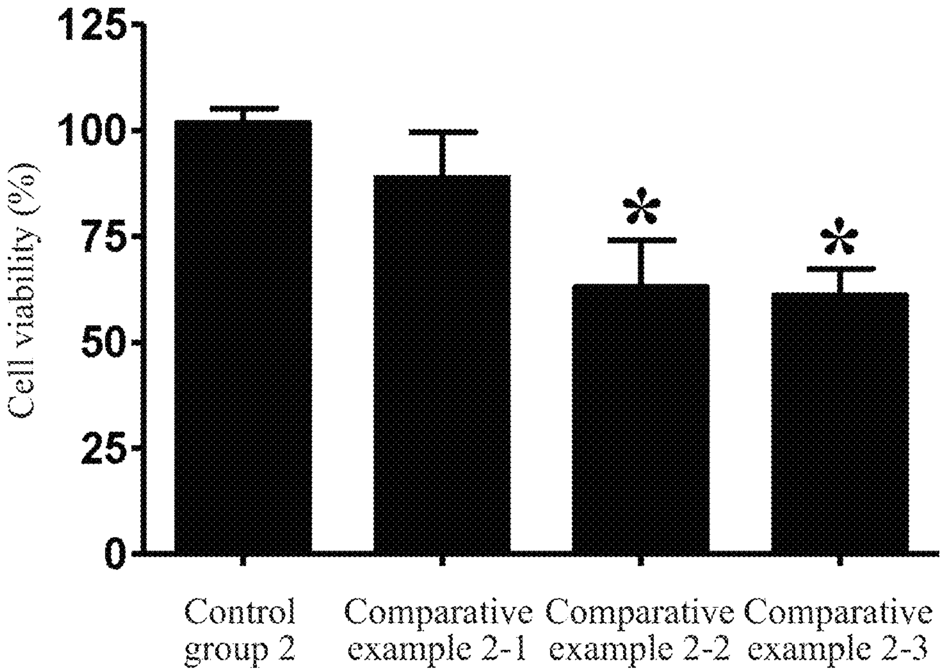
FIG. 3 shows the effect on the cell viability of HFDPC depending on different concentrations of $H_2O_2$.

Please refer to Table 1, Table 2, FIG. 2 and FIG. 3. for the experimental results. FIG. 2 shows the effect on the cell viability of HFDPC depending on different concentrations of tBHP. FIG. 3 shows the effect on the cell viability of HFDPC depending on different concentrations of $H_2O_2$. The control group is the group cultured without peroxide. The comparative example is the group cultured with peroxide. The cell viability is a ratio that the amount of the cells after culture compared to the amount of the cells before culture. The symbol * (P<0.05) indicates a statistically significant difference compared to the control group.

TABLE 1

| | tBHP (μM) | Cell viability (%) |
|---|---|---|
| Control group 1 | — | 98.17 ± 8.1 |
| Comparative example 1-1 | 100 | 88.59 ± 22.1 |
| Comparative example 1-2 | 200 | 82.69 ± 21.7 |
| Comparative example 1-3 | 300 | 59.46 ± 28.7 |

TABLE 2

| | $H_2O_2$ (μM) | Cell viability (%) |
|---|---|---|
| Control group2 | — | 101.83 ± 8.4 |
| Comparative example 2-1 | 100 | 88.9 ± 28.4 |
| Comparative example 2-2 | 300 | 63.05 ± 26.9 |
| Comparative example 2-3 | 500 | 61.14 ± 14.0 |

According to the experimental results, both tBHP and $H_2O_2$ damage HFDPCs. Also, the damage becomes more significant with the concentration increased. In the following experiment, tBHP and $H_2O_2$ are used to induce HFDPCs to be damaged or aged.

Experiment 2: Increasing the Cell Viability of the Damaged Cells

In this experiment, HFDPCs are damaged by 300 μM $H_2O_2$ and 300 μM tBHP and then repaired by the compositions of the embodiments. Also, the recovery of HFDPCs is assessed by Alamar blue cell viability reagent kit and expressed by the cell viability.

Hereinafter, the procedures of the experiment are described. Please refer to the procedures of Experiment 1, $H_2O_2$ or tBHP is added to the wells, and the cells are cultured for 4 hours in the presence of 300 μM $H_2O_2$ or 300 μM tBHP. Then, the supernatant in the wells is removed, and the cells are cultured with the compositions of the embodiments for 8 hours, in which there are 40 μg of the mitochondria and 5% (v/v %) of the plasma in the wells, and the concentration of the mitochondria in the well is 80 μg/mL. Next, the supernatant in the wells is removed, and the cell culture medium is replaced with the medium including Alamar blue and further incubated at 37° C. for 3 to 4 hours. After cell culturing with the medium including Alamar blue, the cell viability is calculated by the fluorescence measured at OD560/590.

Figures 4, 5:
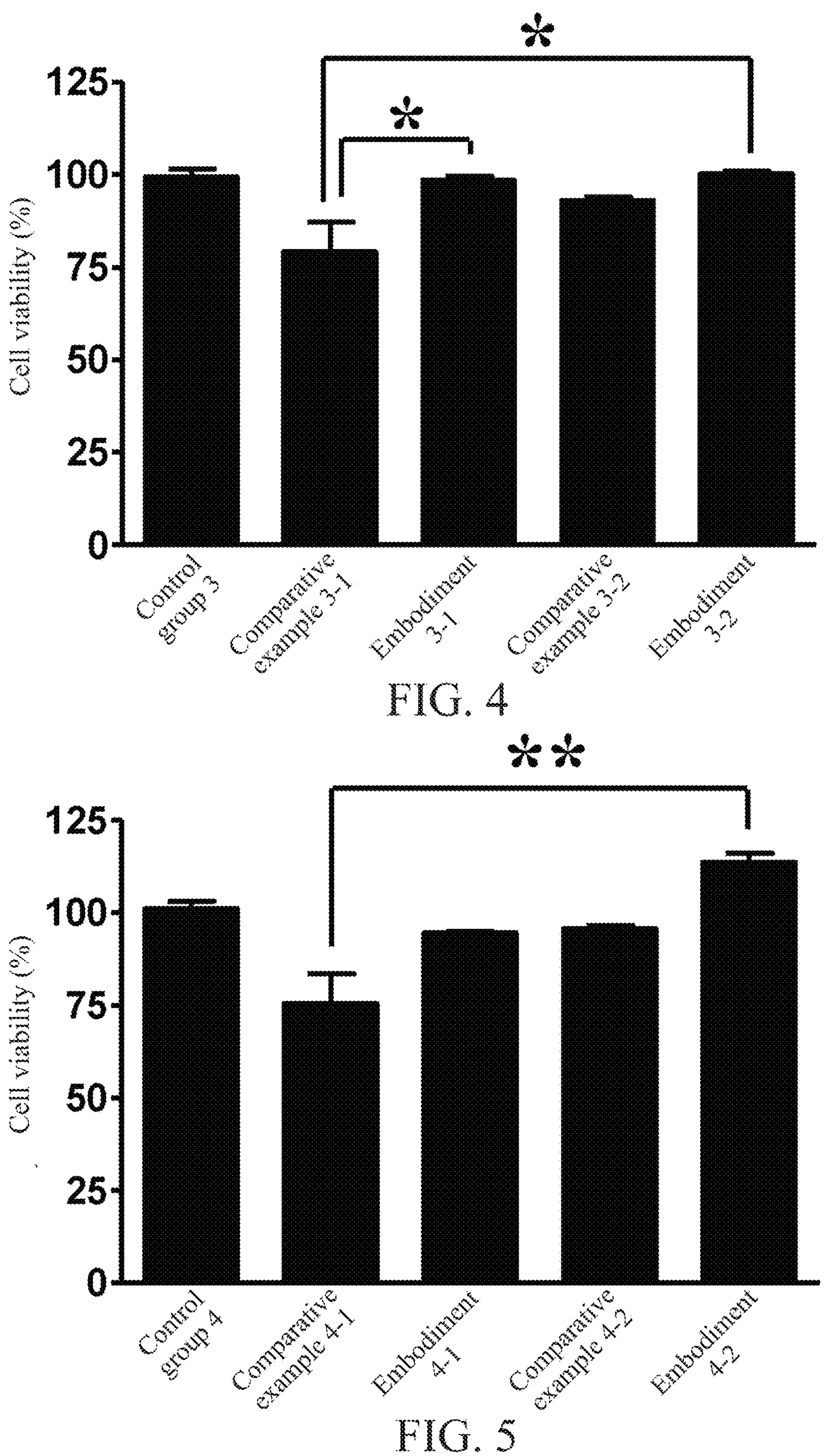
FIG. 4 shows that the cell viability of HFDPC damaged by tBHP is increased by the compositions according to embodiments of the present disclosure.
FIG. 5 shows that the cell viability of HFDPC damaged by $H_2O_2$ is increased by the compositions according to embodiments of the present disclosure.

Please refer to Table 3, Table 4, FIG. 4 and FIG. 5 for the experimental results. FIG. 4 shows that the cell viability of HFDPC damaged by tBHP is increased by the compositions according to embodiments of the present disclosure. FIG. 5 shows that the cell viability of HFDPC damaged by $H_2O_2$ is increased by the compositions according to embodiments of the present disclosure. The control group is the group cultured without peroxide, the plasma, and the mitochondria. The comparative example is the group cultured with peroxide but without the mitochondria. The cell viability is a ratio that the amount of the cells after culture compared to the amount of the cells before culture. The symbol *

(P<0.05) and the symbol ** (P<0.01) indicates a statistically significant difference compared to comparative group.

TABLE 3

| | tBHP (μM) | Mitochondria (μg) | Plasma | Cell viability (%) |
|---|---|---|---|---|
| Control group 3 | — | — | — | 99.34 ± 6.1 |
| Comparative example 3-1 | 300 | — | | 79.02 ± 18.3 |
| Embodiment 3-1 | | 40 | | 98.54 ± 1.8 |
| Comparative example 3-2 | | — | 5% | 92.98 ± 2.4 |
| Embodiment 3-2 | | 40 | | 100.17 ± 1.6 |

TABLE 4

| | $H_2O_2$ (μM) | Mitochondria (μg) | Plasma | Cell viability (%) |
|---|---|---|---|---|
| Control group 4 | — | — | — | 101.1 ± 6.4 |
| Comparative example 4-1 | 300 | — | | 75.48 ± 25.7 |
| Embodiment 4-1 | | 40 | | 94.52 ± 0.7 |
| Comparative example 4-2 | | — | 5% | 95.67 ± 2.0 |
| Embodiment 4-2 | | 40 | | 113.6 ± 4.9 |

According to the experimental results, the composition including mitochondria helps to increase the cell viability, and that means the damage caused by $H_2O_2$ and tBHP can be relieved by the composition, and the composition contributes to cell repair. Also, the composition including the mitochondria and the plasma can further increase the cell viability, and that means the effect of reliving the damage caused by $H_2O_2$ and tBHP and the contribution for cell repair is more significant.

Experiment 3: Cellular Senescence

In this experiment, HFDPCs are induced to be aged by $H_2O_2$ with different concentrations, and the senescence level of HFDPCs is assessed by a SA-03-gal kit and expressed by the cellular senescence level (%).

In the aged cells, senescence-associated beta-galactosidase (SA-β-gal) is overexpressed, and thus SA-β-gal may serve as a biomarker of cellular senescence. The SA-β-gal kit (Senescence β-Galactosidase Staining Kit #9860, Cell Signaling technology) is used in this experiment to evaluate the cellular senescence level.

Hereinafter, the procedures of the experiment are described. HFDPCs after subculture are cultured at a density of $4\times10^4$ cells/1 mL in a 12-well plate for 8 hours. Next, $H_2O_2$ with different concentrations is added to the wells, and the cells are cultured for 4 hours in the presence of $H_2O_2$, in which the concentrations of $H_2O_2$ in the wells are 100 μM, 300 μM, and 500 μM. After cell culture, the cells are washed by PBS, and the senescence level of the cells is assessed by SA-β-gal kit.

Figure 6:
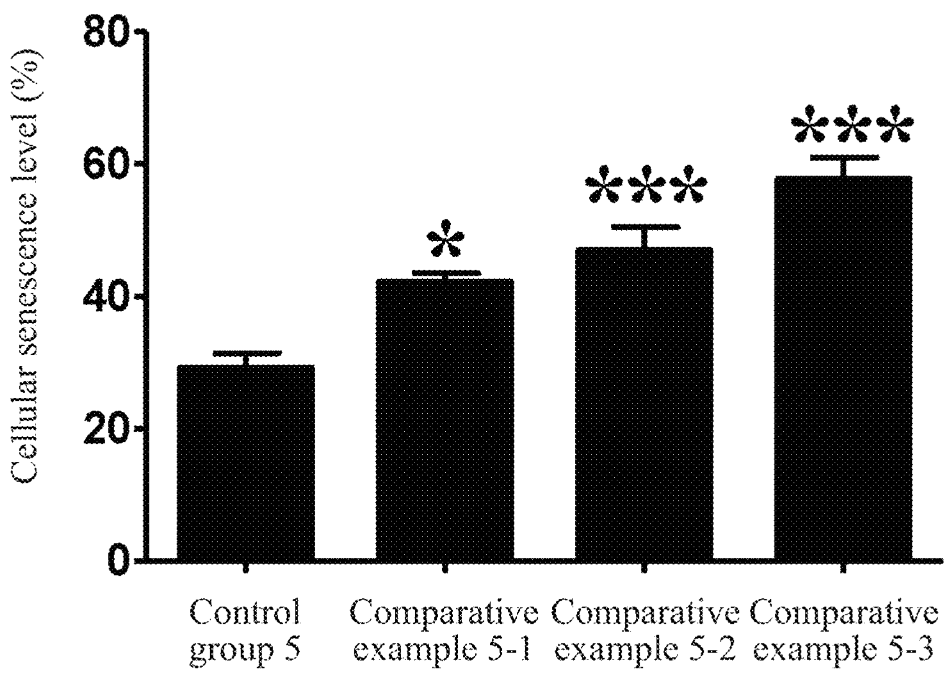
FIG. 6 shows the effect on the cellular senescence level of HFDPC depending on different concentrations of $H_2O_2$.

Please refer to Table 5 and FIG. 6 for the experimental results. FIG. 6 shows the effect on the cellular senescence level of HFDPC depending on different concentrations of $H_2O_2$. The control group is the group cultured without $H_2O_2$. The comparative group is the group cultured with $H_2O_2$. The cellular senescence level is a percentage that the amount of the aged cells compared to the amount of all cells in a unit area. The symbol * (P<0.05), the symbol  (P<0.01), and the symbol * (P<0.001) indicates a statistically significant difference compared to the control group.

TABLE 5

| | $H_2O_2$ (μM) | Cellular senescence level (%) |
|---|---|---|
| Control group5 | — | 29 ± 6.1 |
| Comparative example 5-1 | 100 | 42 ± 2.5 |
| Comparative example 5-2 | 300 | 47 ± 6.9 |
| Comparative example 5-3 | 500 | 58 ± 6.4 |

According to the experimental results, $H_2O_2$ causes aging damage to HFDPC. Also, the cellular senescence level becomes more significant with the $H_2O_2$ concentration increased. In the following experiment, 300 μM $H_2O_2$ is used to induce HFDPC to be aged.

Experiment 4: Decreasing the Cellular Senescence Level

In this experiment, HFDPCs are aged by 300 μM $H_2O_2$ and then repaired by the compositions of the embodiments. Also, the effect of the compositions of the embodiments on senescence of HFDPC is assessed by a SA-β-gal kit and expressed by the cellular senescence level (%).

Hereinafter, for the procedures of the experiment, please refer to the procedures of Experiment 3. First, $H_2O_2$ is added to the wells, and the cells are cultured for 4 hours in the presence of 300 μM $H_2O_2$. Then, the supernatant in the wells is removed, the cells are washed with PBS and cultured with the compositions of the embodiments for 8 hours, in which there are 40 μg of the mitochondria and the 5% (v/v %) of the plasma in the wells, and the concentration of the mitochondria in the well is 40 μg/mL. After cell culture, the cells are washed by PBS, and the cellular senescence level is assessed by a SA-β-gal kit.

Figure 7:
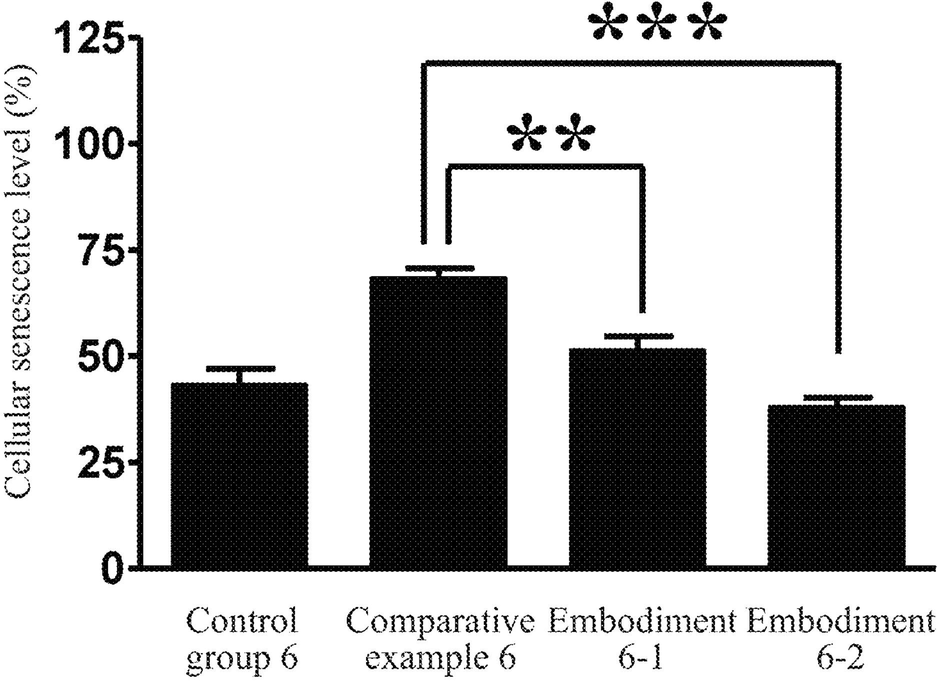
FIG. 7 shows that the cellular senescence level of HFDPC damaged by $H_2O_2$ is decreased by the compositions according to embodiments of the present disclosure.

Please refer to Table 6 and FIG. 7 for the experimental results. FIG. 7 shows that the cellular senescence level of HFDPC damaged by $H_2O_2$ is decreased by the compositions according to embodiments of the present disclosure. The control group is the group cultured without $H_2O_2$, the plasma, and the mitochondria. The comparative group is the group cultured with $H_2O_2$ but without the mitochondria. The cellular senescence level is a percentage that the amount of the aged cells compared to the amount of all cells in a unit area. The symbol * (P<0.05), the symbol  (P<0.01), and the symbol * (P<0.001) indicates a statistically significant difference compared to the comparative group.

TABLE 6

| | $H_2O_2$ (μM) | Mitochondria (μg) | Plasma | Cellular senescence level (%) |
|---|---|---|---|---|
| Control group 6 | — | — | — | 43 ± 10.02 |
| Comparative example 6 | 300 | — | | 68 ± 6.3 |
| Embodiment 6-1 | | 40 | | 51 ± 8.6 |
| Embodiment 6-2 | | 40 | 5% | 38 ± 5.8 |

According to the experimental results, the composition including the mitochondria contribute to decreasing the cellular senescence level, and that indicates the composition can effectively relieve the cellular senescence level and contribute to cell repair. Also, the composition including the mitochondria and the plasma can further relieve the cellular senescence level, and that indicates the effects of cell repair and relieving cellular senescence are more significant.

Experiment 5: Repairing Cell Oxidative Damage

In this experiment, HFDPCs are induced to be oxidative damaged by 300 μM tBHP and then repaired by the compositions of the embodiments. Also, the effect of the compositions of the embodiments on oxidative pressure of HFDPC is assessed by 2',7'-dichlorodihydrofluorescein diacetate (DCFDA) and expressed by fluorescence.

DCFDA is a fluorescent substance having four benzene rings. DCFDA may pass through the cell membrane and remain in the cell due to the reaction of removing ethyl carboxyl group by esterase in the cell. DCFDA may react with radicals in the cells and emit fluorescence. The more radicals mean the higher oxidative pressure, and it may induce the fluorescence with higher intensity. Therefore, DCFDA is usually served as the fluorescent substance for detecting radicals. DCFDA is used in this experiment to evaluate the oxidative pressure of cells.

Hereinafter, the procedures of the experiments are described. HFDPCs after subculture are cultured at a density of $2.5\times10^4$ cells/200 μL in a 96-well plate for 8 hours. Next, tBHP is added to the wells, the cells are cultured for 4 hours in the presence of tBHP, in which the concentration of tBHP in the wells is 300 μM. Next, the supernatant in the wells is removed, and the cells are washed by PBS and cultured with the compositions of the embodiments for 8 hours, in which there are 1 μg, 15 μg, and 40 μg of mitochondria in the well, and the concentrations of the mitochondria in the wells are 5, 75, 200 μg/mL, respectively. After cell culture, the cells are washed by PBS and reacted with medium including 25 μM DCFDA for 30 minutes at 37° C. After reaction, the cells are washed by PBS and added with fresh cell culture medium, and the fluorescence from the cells are measured at OD485/535.

Figure 8:
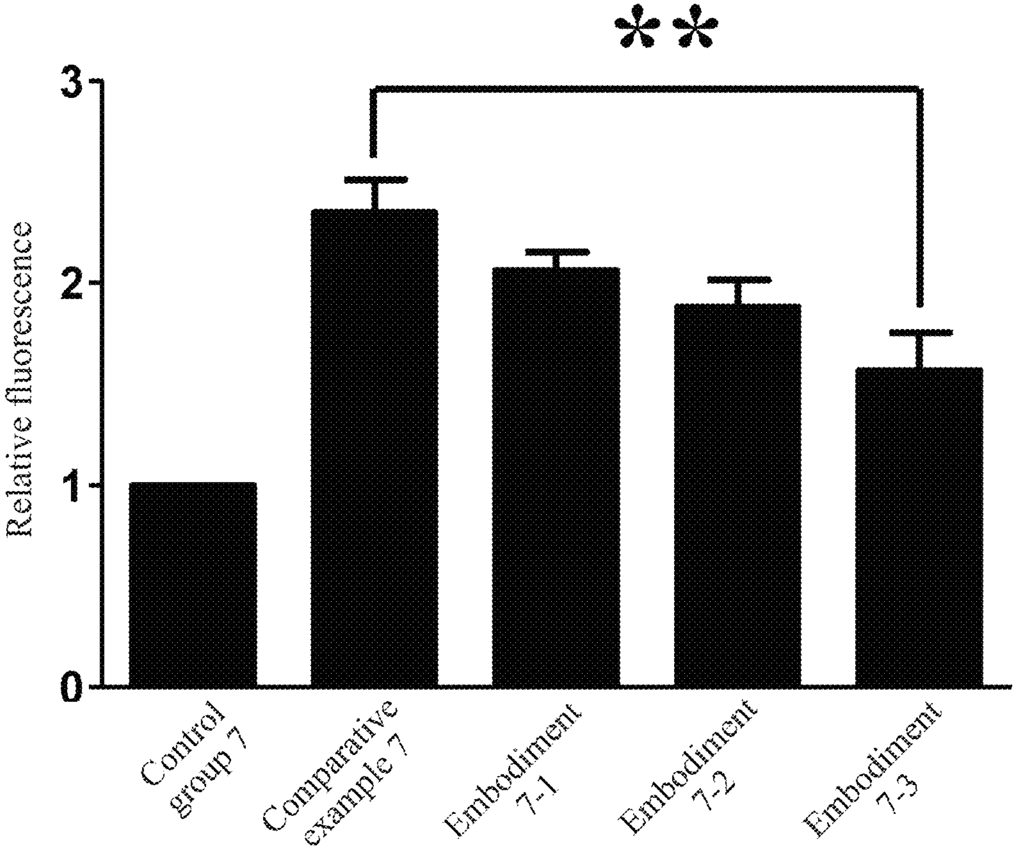
FIG. 8 shows that the oxidative damage of HFDPC is repaired by the compositions according to embodiments of the present disclosure.

Please refer to Table 7 and FIG. 8 for the experimental results. FIG. 8 shows that the oxidative damage of HFDPC is repaired by the compositions according to embodiments of the present disclosure. The control group is the group cultured without peroxide and mitochondria. The comparative group is the group cultured with peroxide but without the mitochondria. The vertical axis is relative fluorescence, which indicates the fluorescence intensity compared to that of the control group, set as 1. The symbol ** ($P<0.01$) indicates a statistically significant difference compared to comparative group.

TABLE 7

| | tBHP (μM) | Mitochondria (μg) | Relative fluorescence |
|---|---|---|---|
| Control group 7 | — | — | 1 |
| Comparative example 7 | 300 | — | 2.51 ± 0.46 |
| Embodiment 7-1 | | 1 | 2.06 ± 0.16 |
| Embodiment 7-2 | | 15 | 1.88 ± 0.23 |
| Embodiment 7-3 | | 40 | 1.57 ± 0.33 |

According to the experimental results, the composition including mitochondria contributes to reducing radicals in the cells, and that indicates it may effectively reduce the oxidative pressure and repair the oxidative damage of the cells so as to contribute to cell repair. Also, as the concentration of the mitochondria increases, the reducing of radicals is more significant, and that indicates the effect of repairing oxidative damage is also increased.

Experiment 6: Mice Experiment

In this experiment, an animal experiment is performed with mice and tBHP. After the mice receive tBHP-induced damage, the skin and hair growth condition of the mice treated with or without the compositions of the embodiments are observed.

Hereinafter, the procedures of the experiment are described. C57BL/6 mice (male, 35 days old, Day 35) are used and anesthetized with 2% isoflurane by a gas anesthesia machine. The hair of the mice's back is shaved by an electronic shaver and disinfected with 75% alcohol. Then, 100 μL of 300 μM tBHP is injected subcutaneously into the mice's back by insulin injection needles (BD VeoTMinslin syringes). Injection is performed once a day for 5 days. Then, 100 μL of the composition of the embodiment is administered by subcutaneous injection. Injection of the composition is performed once a day for 3 days. The skin and hair growth condition is observed on 6 days after the injection of the composition (Day 49).

Next, after sacrificing the mice, the back skin of the mice is taken to perform the frozen tissue embedding. In detail, the skin tissue is taken to 4% of formaldehyde fixation fluid, swayed at 4° C. for 4 to 6 hours. After removing the 4% of formaldehyde fixation fluid, the skin tissue is moved to 15% of sucrose solution, swayed at 4° C. for 6 to 8 hours. After removing the 15% of sucrose solution, the skin tissue is moved to 30% of sucrose solution, swayed at 4° C. overnight. The skin tissue is taken out from the solution and moved to the embedding cassette, and OCT frozen embedding fluid (23-730-571, Thermo Fisher Scientific) is added to perform embedding. The embedded tissue is stored at −80° C. The skin tissue is cryosectioned, the thickness of the frozen section is about 15 to 20 μm, and the sectioned tissue is stored at −80° C.

Next, the sectioned tissue is dyed by fluorescence. In detail, the tissue for section is taken out from −80° C. and placed at room temperature to warm up and then rinsed with PBS twice, 5 minutes for each. Next, 1% of Bovine serum albumin (BSA) prepared in PBS-T (PBS containing 0.4% of triton X-100) is used for rinsing the tissue twice, 10 minutes for each. Next, 1% of BSA prepared in PBS-T is used for blocking and reacted with the tissue for at room temperature 30 minutes so as to block nonspecific substance and increase sensitivity and specificity of anti-body. Next, 1% of BSA prepared in PBS-T is used for rinsing the tissue twice, 10 minutes for each. Next, anti-body F4/80 (#MA5-16624, Thermo Fisher Scientific) is prepared in PBS-T of 1% of BSA at a ratio of 1:50 and used to react with the tissue at room temperature for 1.5 hours. Next, 1% of BSA prepared in PBS-T is used for rinsing the tissue twice, 10 minutes for each. Next, Alexa Fluor®594 (goat anti rat secondary conjugation Alexa Fluor®594, ab150160, abcam) is prepared in PBS-T of 1% of BSA at a ratio of 1:200 and used to react with the tissue at room temperature for 1 hour. Next, 1% of BSA prepared in PBS-T is used for rinsing the tissue twice, 10 minutes for each. Next, DAPI (D1306, Thermo Fisher Scientific) is used to react with the tissue at room temperature for 5 minutes for nucleus staining. Finally, pictures are taken with a fluorescence microscope.

Figures 9, 10:
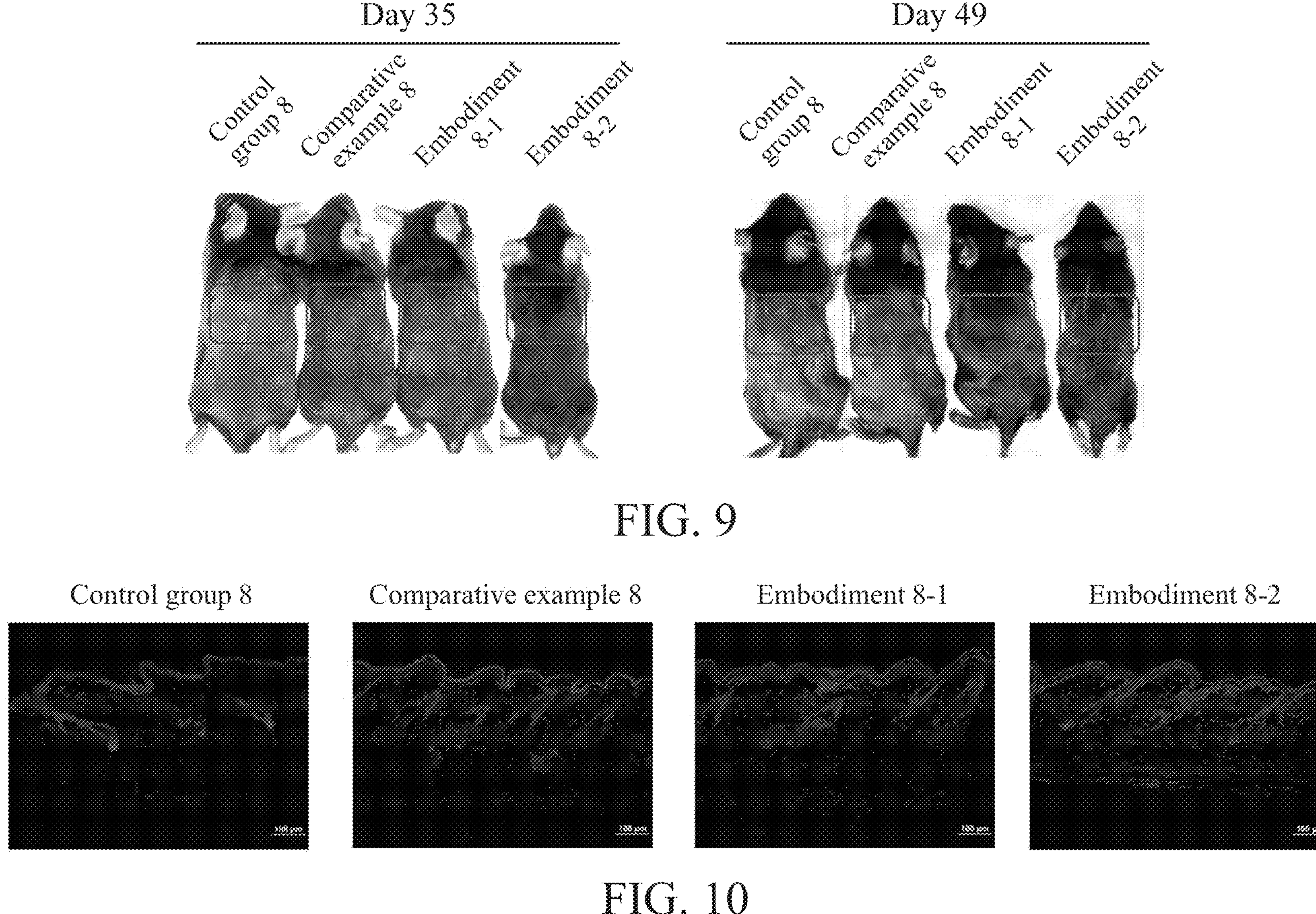
FIG. 9 shows the hair growth of mice's backs treated with the compositions according to embodiments of the present disclosure.
FIG. 10 shows the frozen tissue sections of the mice of FIG. 9.
Figure 11:
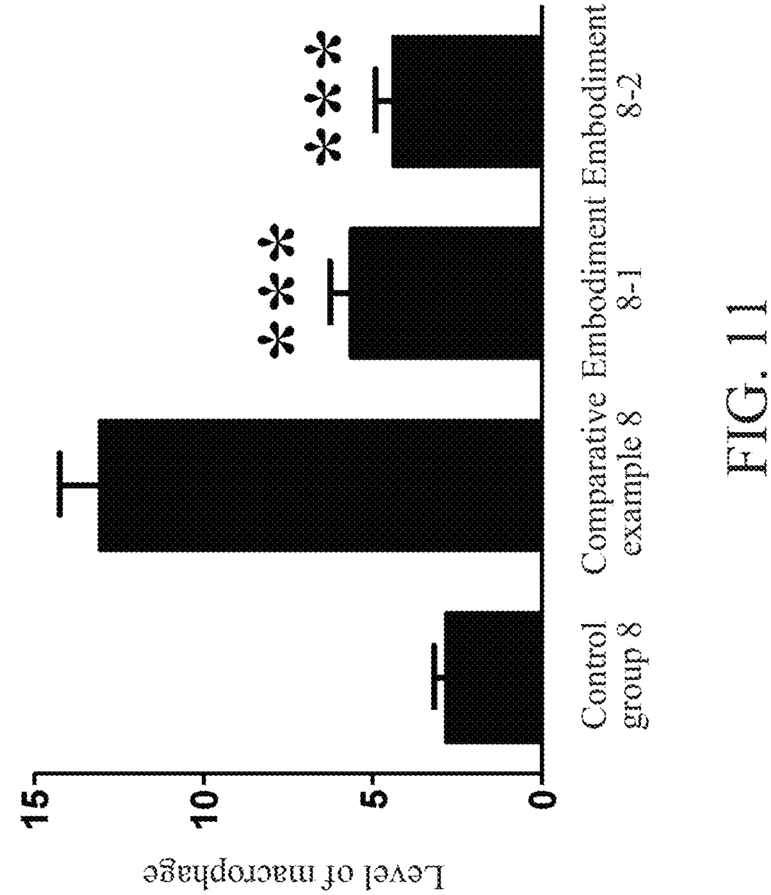
FIG. 11 shows the level of macrophages in the sections of FIG. 10.

Please refer to Table 8 and FIG. 9 to FIG. 11 for the experimental results. FIG. 9 shows the hair growth of mice's backs treated with the compositions according to embodiments of the present disclosure. FIG. 10 shows the frozen tissue sections of the mice of FIG. 9. FIG. 11 shows the number of macrophages in the sections of FIG. 10. The control group is the group without administration of tBHP and the composition of the embodiment.

The comparative group is the group without administration of the composition of the embodiment. Embodiment 8-1 is the group with administration of the composition including 40 μg of the mitochondria (400 μg/mL). Embodiment 8-2 is the group with administration of the composition including 40 μg of the mitochondria (400 μg/mL) and 5% (v/v %) of the plasma. The symbol *** (P<0.001) indicates a statistically significant difference compared to comparative group.

TABLE 8

| | tBHP (μM) | Mitochondria (μg) | Plasma | Level of macrophages |
|---|---|---|---|---|
| Control group 8 | — | — | — | 2.81 ± 0.67 |
| Comparative group 8 | 300 | — | | 13.05 ± 2.43 |
| Embodiment 8-1 | | 40 | | 5.63 ± 1.28 |
| Embodiment 8-2 | | 40 | 5% | 4.37 ± 1.1 |

As seen from the picture of FIG. 9, compared to the control group and the embodiments, the mice's back of the comparative example is relatively red, which indicates inflammation occurs in the skin and the hair follicles of the mice. Compared to the comparative example, the mice administrated with the composition including the mitochondria or the composition including the mitochondria and the plasma have backs that present relatively dark and without redness. This indicates the inflammation is obviously relieved, and the hair follicles start to grow hair since the damage is relieved.

In FIG. 10, the blue indicates the dyed nucleus, and the blue area presents the morphology of the hair follicles; the red indicates the dyed macrophages, and the red area presents the area in which macrophages gather and also presents the inflammation position. As seen from the section picture of FIG. 10, the density of the red of the comparative group is obviously more than that of the embodiments, and this indicates that the mice of the comparative group are induced to have damaged and inflamed hair follicles by tBHP so that the macrophages gather at the hair follicles. The mice administrated with the composition including the mitochondria or the composition including the mitochondria and the plasma have obviously less red at the hair follicles, and this indicates the macrophages obviously decreases at the hair follicles and also indicates inflammation is obviously relieved.

FIG. 11 and Table 8 present the analysis of the section image of FIG. 10 by Image J quantitative software. The level of macrophages is the fluorescence expression in a unit area analyzed by Image J quantitative software and expressed by the product of the area and fluorescence intensity. The higher level of macrophages means inflammation is more serious. From the fluorescence analysis, it is further confirmed that the level of macrophageis obviously decreased in the mice administrated with the composition including the mitochondria or the composition including the mitochondria and the plasma, and that indicates inflammation is obviously relieved. Also, the composition including the mitochondria and the plasma has a more excellent effect on relieving inflammation.

Experiment 7: Mice Experiment for Mitochondria-Rich Plasma

In this experiment, an animal experiment is performed with mice and tBHP. After the mice receive tBHP-induced damage, the skin and hair growth condition of the mice treated with or without the compositions of the embodiments are observed.

Please refer to Experiment 6 for the experimental procedures. The composition used in this experiment is mitochondria-rich plasma.

Figures 12, 13:
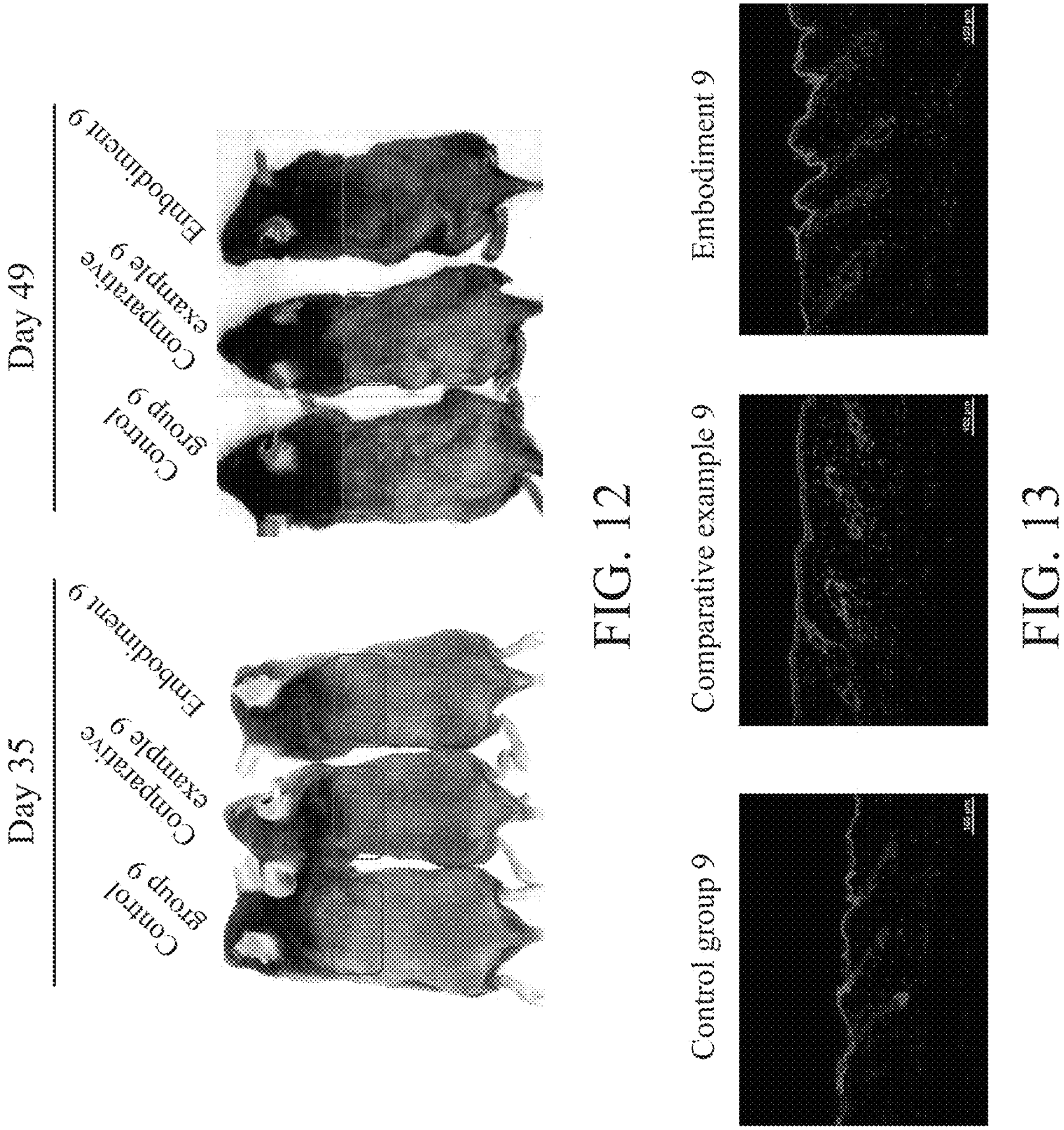
FIG. 12 shows the hair growth of mice's backs treated with the compositions according to embodiments of the present disclosure.
FIG. 13 shows the frozen tissue sections of the mice of FIG. 12.
Figure 14:
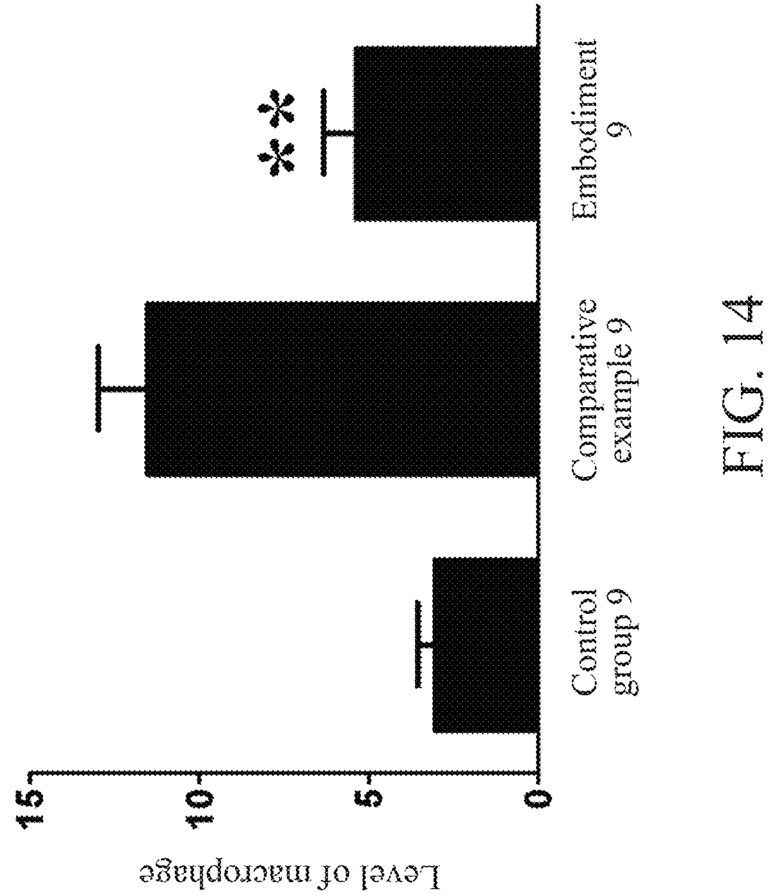
FIG. 14 shows the level of macrophages in the sections of FIG. 13.

Please refer to Table 9 and FIG. 12 to FIG. 14 for the experimental results. FIG. 12 shows the hair growth of mice's backs treated with the compositions according to embodiments of the present disclosure. FIG. 13 shows the frozen tissue sections of the mice of FIG. 12. FIG. 14 shows the level of macrophages in the sections of FIG. 13. The control group is the group without administration of tBHP and the composition of the embodiment. The comparative group is the group without administration of the composition of the embodiment. Embodiment 9 is the group with administration of the composition including the mitochondria-rich plasma. The symbol ** (P<0.01) indicates a statistically significant difference compared to comparative group.

TABLE 9

| | tBHP(μM) | Mitochondria-rich plasma | Level of macrophages |
|---|---|---|---|
| Control group 9 | — | – | 3.03 ± 1.04 |
| Comparative example 9 | 300 | – | 11.51 ± 2.97 |
| Embodiment 9 | | + | 5.36 ± 1.97 |

As seen from the picture of FIG. 12, compared to the control group and the embodiment, the mice's back of the comparative example is relatively red, which indicates inflammation occurs in the skin and the hair follicles of the mice. Compared to the comparative example, the mice administrated with the composition including the mitochondria-rich plasma has its back that present relatively dark and without redness. This indicates the inflammation is obviously relieved, and the hair follicles start to grow hair since the damage is relieved.

In FIG. 13, the blue indicates the dyed nucleus, and the blue area presents the morphology of the hair follicles; the red indicates the dyed macrophages, and the red area presents the area in which macrophages gather and also presents the inflammation positions. As seen from the section picture of FIG. 13, the density of the red of the comparative group is obviously more than that of the embodiment and the control group, and this indicates that the mice of the comparative group are induced to have damaged and inflamed hair follicles by tBHP so that the macrophages gather at the hair follicles. The mice administrated with the composition including the mitochondria-rich plasma shows obviously less red at the hair follicles, and this indicates less macrophages at the hair follicles and also indicates inflammation is obviously relieved.

FIG. 14 and Table 9 present the analysis of the section image of FIG. 13 by Image J quantitative software. From the fluorescence analysis, it is further confirmed that the level of macrophages is obviously decreased in the mice administrated with the composition including the mitochondria-rich plasma, and that indicates inflammation is obviously relieved.

Experiment 8: Experiment on the Scalp for Mitochondria-Rich Plasma

In this experiment, a micro wound on the scalp is generated by a micro pin, and the composition including the mitochondria-rich plasma is applied on the scalp. An appropriate amount of the composition including the mitochondria-rich plasma is taken and uniformly applied to cover the wound. The applying range is about 25 to 49 $cm^2$. On day before applying and 60 days after applying, the condition of hair growth is observed, and the pixel thereof is analyzed.

Figures 15, 16:
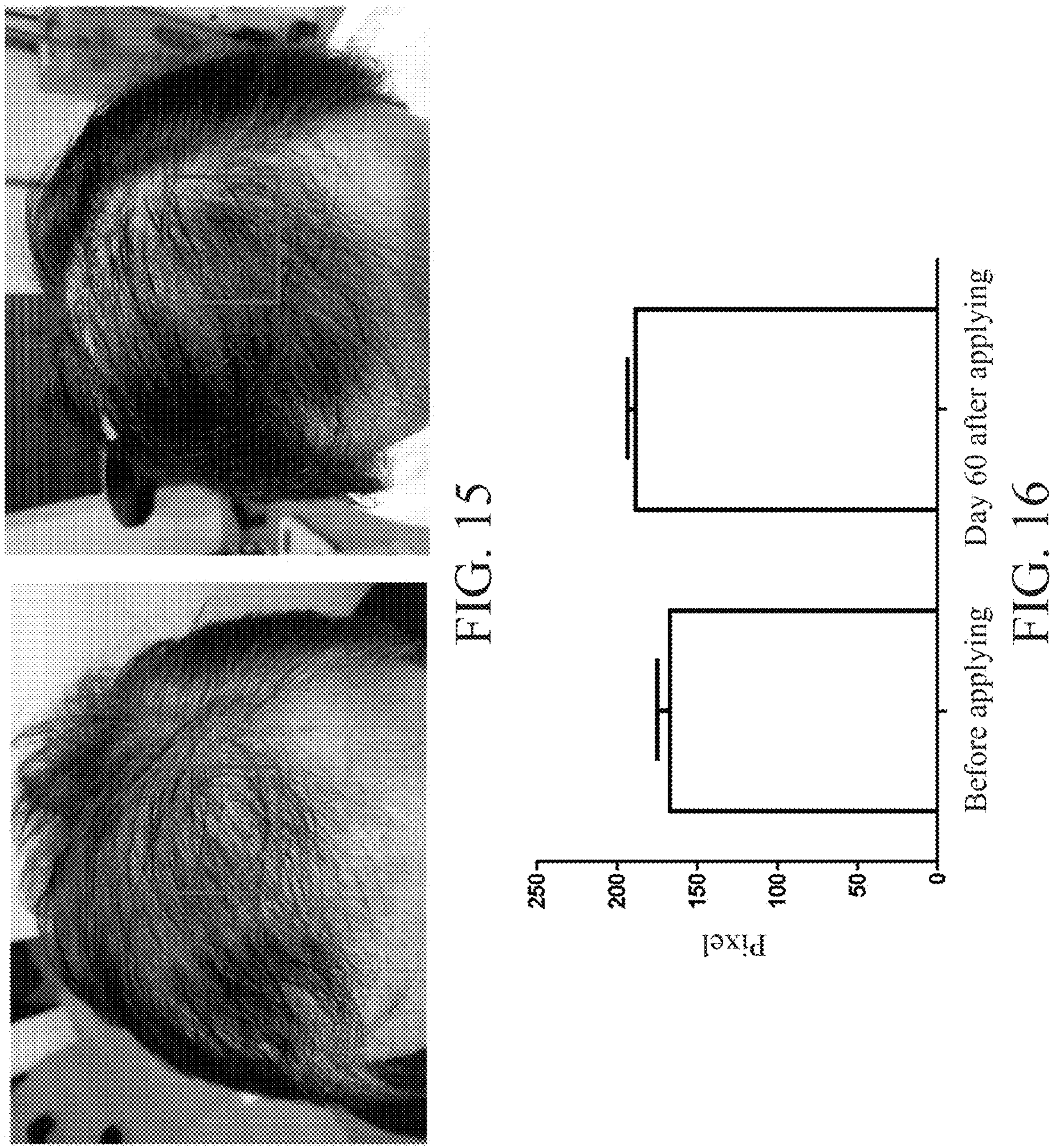
FIG. 15 shows the hair growth before and after applying the composition according to one embodiment of the present disclosure on the scalp.
FIG. 16 shows the pixel analysis of the scalp of FIG. 15.

Please refer to Table 10 and FIG. 15 to FIG. 16 for the experimental results. FIG. 15 shows the hair growth before and after applying the composition according to one embodiment of the present disclosure on the scalp. FIG. 16 shows the pixel analysis of the scalp of FIG. 15. The pixel of the vertical axis represents the amount of the hair in a unit area, and the density of hair is expressed by pixel.

TABLE 10

| Time | Pixel |
|---|---|
| Before applying | 167.2 ± 13.7 |
| Day 60 after applying | 188.4 ± 8.9 |

As seen from the picture of FIG. 15 and FIG. 16, the density of hair increases 60 days after applying the composition of the embodiment, and this indicates that the composition including the mitochondria-rich plasma indeed contributes to hair growth.

In view of the above description, mitochondria-rich plasma can be manufactured by a method of the present disclosure, and providing mitochondria or the mitochondria-rich plasma to hair follicles can help cells in the hair follicles grow so as to promote hair regrowth. For damaged cells, the cell viability can be increased. For aged cells, the cellular senescence level can be relieved. For cells damaged by radicals, the oxidative damage can be relieved. In addition, the inflammation of hair follicles can be relieved by supplying or injecting the composition comprising mitochondria or the mitochondria-rich plasma to the skin around the hair follicles.

What is claimed is:

1. A method for manufacturing mitochondria-rich plasma, comprising:

separating plasma and cells from blood;

taking out mitochondria from the cells; and mixing the plasma and the mitochondria to form mitochondria-rich plasma;

wherein a weight of the mitochondria in the mitochondria-rich plasma is 40 μg, a concentration (v/v %) of the plasma is 5%, and the mitochondria and the plasma are derived from the same batch of blood of the same individual, the mitochondria-rich plasma comprises platelets and growth factors, the growth factors comprises at least one selected from the group consisting of at least 3.1 mg/ml of TGF-β1, at least 9.5 ng/mL of PDGF-AA, at least 91.7 ng/ml of PDGF-AB, and at least 79.3 ng/ml of PDGF-BB, and a number of the platelets in the plasma is less than $1\times10^4$ per μL.

2. The method of claim 1, wherein the step of separating plasma and cells from blood comprises:

stratifying the blood to form an erythrocyte layer, a buffy coat layer, and a plasma layer; and taking out the buffy coat layer and the plasma layer;

the step of taking out mitochondria from the cells comprises:

taking out the mitochondria from the cells in the buffy coat layer; and the step of mixing the plasma and the mitochondria comprises:

mixing the plasma layer and the mitochondria.

3. The method of claim 1, wherein a concentration of the mitochondria in the mitochondria-rich plasma is 5 μg/mL to 200 μg/mL.

* * * * *